United States Patent [19]

Sandhaus

[11] Patent Number: 4,466,796
[45] Date of Patent: Aug. 21, 1984

[54] DENTAL IMPLANT FOR USE AS A PILLAR IN A MOUTH

[75] Inventor: Sami Sandhaus, Lausanne, Switzerland

[73] Assignee: CBS Biotechnic SA, Switzerland

[21] Appl. No.: 312,824

[22] Filed: Oct. 19, 1981

[30] Foreign Application Priority Data

Oct. 20, 1980 [CH] Switzerland .................... 7810/80

[51] Int. Cl.³ ............................................... A61C 8/00
[52] U.S. Cl. .................................................. 433/173
[58] Field of Search ........................ 433/174, 175, 173

[56] References Cited

U.S. PATENT DOCUMENTS 3,579,830  5/1971  Morel ................................. 433/176
3,672,058  6/1972  Nikoghossian ..................... 433/176
4,060,896 12/1977  Wahnish ............................. 433/174
4,079,515  3/1978  Friedman ........................... 433/173
4,229,169 10/1980  Smith et al. ........................ 433/174

FOREIGN PATENT DOCUMENTS 2308348  4/1975  France ................................ 433/174
2,063,680 11/1979  United Kingdom ............... 433/174

OTHER PUBLICATIONS

Kawalara et al., of Ser. No. 89,781 filed Sep. 7, 1972, published in vol. 81, 1974, p. 434.

Primary Examiner—Robert Peshock
Attorney, Agent, or Firm—Ostrolenk, Faber, Gerb & Soffen

[57]  ABSTRACT

The dental implant comprises a head, preferably having a polygonal section like a hexagonal one; a generally central portion provided with a specially shaped thread; and a rear portion which is tapered and provided with a slot over the diameter of the ending surface. The implant is made from bioceramics and adapted to be screwed in a hole previously drilled into the patient's maxillary bone.

6 Claims, 4 Drawing Figures

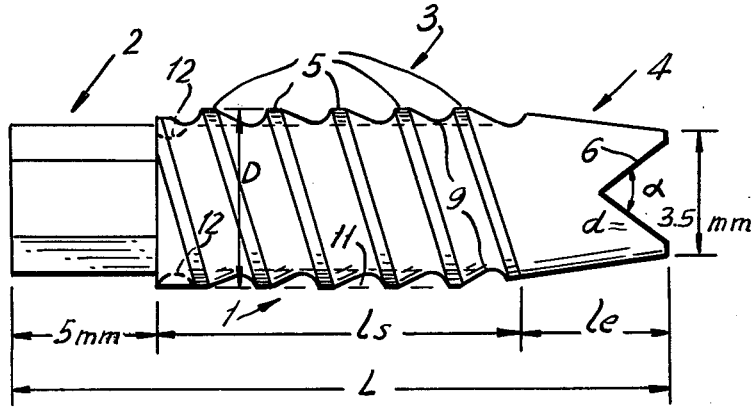
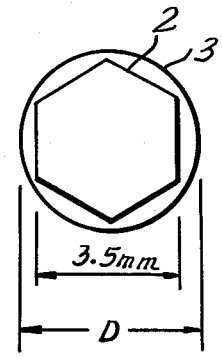
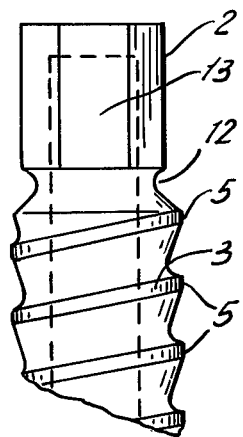
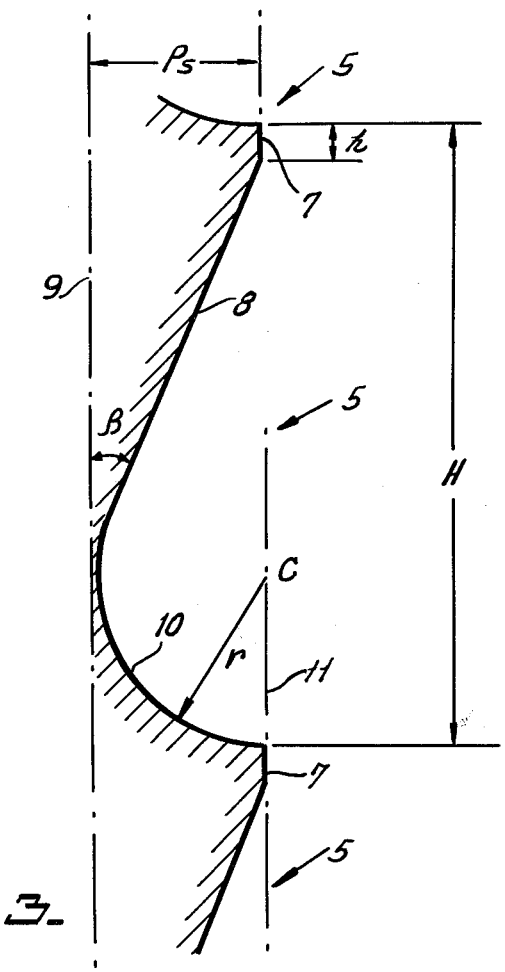

DENTAL IMPLANT FOR USE AS A PILLAR IN A MOUTH

BACKGROUND OF THE INVENTION

1. Field of the invention

This invention is in the field of dental surgery. More specifically, it is related to a dental implant which is to serve as a pillar or tenon in the mouth of a person, said implant having a head and a central portion provided with a thread.

2. Description of the Prior Art

Dental implants are nowadays currently used in dental surgery for creating pillars which serve as a support for dental prothesis. Generally, such implants are screwed into holes which the surgeon drills into the jawbone of a patient wherein the implant should be fixed by ossification. More details of this special field can be found in the book "Nouveaux aspects de l'Implantologie", Lausanne (Switzerland) 1969, by Dr. S. Sandhaus.

Implants having a threaded body are available on the market. However, these known implants suffer from certain disadvantages which hinder them from fulfilling the function for which they have been designed. When these implants are made of metal, they will generally be attacked by the constant contact with the oral liquids, e.g. saliva, blood, etc., and/or they provoke rejection phenomena. Even if this is not the case, they remain seldom strongly anchored in the patient's jaw.

SUMMARY OF THE INVENTION

It is therefore an object of the present invention to provide an implant which does not create any phenomenon of rejection. Another important object of the invention is to provide such an implant which will remain strongly anchored in the jaw wherein it has been screwed. Other objects of the invention will be developped in the following description.

These objects are met by the implant of the invention having a head and a central, threaded portion, wherein said central portion is followed by a rear portion which is tapered and provided with a slot. This slot extends substantially over the whole diameter of the end of said rear portion. Said rear slot may be formed as a V notch where the V has an opening angle of about 60°. The central portion of the implant is of general cylindrical form.

The thread turns or spires will preferably have a supporting surface which will enter in strong contact with the walls of the hole previously drilled into the patient's jaw. This first, cylindrical portion is followed by a second, truncated conic portion which is continued by a third, circular arc portion. This circular arc portion ends in the next contact surface. This special form of the thread is a preferred feature of the invention.

The head which may have a polygonal section, has a normal length of about 5 mm.

The implant preferably has a total length of about 20 mm and a diameter of about 5 mm, the central portion bearing at least about five complete thread turns. The thread pitch is preferably about 2 mm. Another preferred implant has a total length of about 15 mm, a diameter of about 4 mm, at least about seven complete screw turns, a thread pitch of about 1.5 mm, and a thread depth of about 0.25 mm.

The above-mentioned and other features and objects of this invention and the manner of attaining them will become more apparent and the invention itself will be better understood by reference to the following description of embodiments thereof taken in conjunction with the accompanying drawing.

BRIEF DESCRIPTION OF THE DRAWING

FIG. 1 is a side view partly in longitudinal section of a first embodiment of an implant according to the invention, FIG. 2 is a top view, looking from the left of the implant represented in FIG. 1, FIG. 3 is an enlarged, partial view of a section in the longitudinal axis of the implant of FIG. 1, showing the thread shape, and FIG. 4 is a view corresponding to a portion of that of FIG. 1 in partial longitudinal section of a variant of the implant shown in FIGS. 1 to 3.

The implant 1 (FIGS. 1 and 2) has a head 2, a generally cylindrical central portion 3 provided with external threads, and an end portion 4 tapered against its end.

The head 2 of the represented implant has generally a height of 5 mm and a distance between opposite hexagonal head surfaces of about 3.5 mm. It will be understood that the implant of FIGS. 1 to 3 can be made in numerous variants as to the length, the diameter of the central portion, the number of thread turns, etc.; however, it is preferred that the head 2 is standardized to a height of 5 mm and a distance between opposing hexagonal surfaces of 2.5 mm in order to enable its manipulation with the same tools, especially the same wrenches. The model shown in FIG. 1 to FIG. 3 has a diameter D of about 5 mm and a total length L of about 20 mm. As shown in FIG. 1, it has five full threads 5 which extend over a length $l_s$ of about 10 mm. The rear portion 4 begins at the last thread turn and has a length $l_e$ of about 5 mm and is tapered until a final diameter d of about 3.5 mm. A slot in the form of a notch 6 is provided at the final diameter and has an inner angle $\alpha$ of about 60°. The notch 6 extends as profoundly as possible into the implant, taking of course into account the solidity requirements of the remaining wall portions. The notch has a depth of at least 1 mm in the shown embodiment where the total length L is about 20 mm. In FIG. 1, the five threads 5 are shown on the surface of the implant. They have a depth $P_s$ of about 0.55 mm (see FIG. 3) and a pitch H of about 2 mm. Going downward over the implant, the thread turns 5 are composed of a cylindrical surface area 7 having a truncated conical surface area 8 having an opening angle $\beta$ of about 23° with the axis of the implant. This truncated conical surface extends towards the interior of the implant until a distance $P_s = 0.55$ mm from the cylindrical surface portion 7, represented by the dashed line 9. The conical surface 8 is followed by a circular arc surface area 10; the center C of the circle is placed on the mantle surface 11 of the cylinder formed by the surface portions 7, and the radius r of the circle is about 0.5 mm. This circular arc surface 10 is finally followed by the cylindrical surface area 7 of the downwardly next, adjacent turn of the thread.

This special thread form now described, combined with the indicated dimensions and the number of thread turns, especially L=20 mm, D=5 mm and $\alpha=60°$, results in a particularly well adapted implant for use in the human mouth.

As already mentioned, the inventor will not limit himself to the implant shown, having a diameter of 5 mm, and its manufacture. He provides of course a set of several implant models or embodiments having varying sizes, shapes and dimensions so that the surgeon may select a particular model depending upon the patient's mouth, its geometry and the particular place where the implant is to be fixed. At least four models are proposed, namely two implants having a diameter of 5 mm, and two other implants having a diameter of 4 mm.

The first model (D=5 mm, L=20 mm) has been described with reference to FIGS. 1 and 2. The second model has a diameter of 5 mm but a length L of only 15 mm. In this variant, the head 2 and the rear portion 4 have a length of 5 mm each, and the central portion 3 has a length $L_s$ of only 5 mm. Therefore, it is provided with 2½ thread turns only, the pitch H being still 2 mm and the depth $P_s$ 0.55 mm.

On these bases, the inventor has realized a third and fourth implant where the diameter D is only 4 mm. These two embodiments are not represented in the drawing since they are substantially similar to the embodiment shown in FIGS. 1 to 3, with the only exception that the diameter D is 4 mm (instead of 5 mm), the lengths L being 20 and 15 mm, respectively. They have both hexagonal heads as shown. The number of thread turns is seven and 3½ complete turns, respectively, the pitch H being 1.5 mm and the depth $P_s$ 0.25 mm. The section of the threads closely corresponds to that shown in FIG. 3, the surface 7 having a height h of 0.1 mm, r being 0.2 mm, and d 2.6 mm (see FIG. 1).

The four implant embodiments just described have a very sophisticated shape being the fruit of several years of effort and experiments. This particular shape has nothing of hazard but rather is the logical outcome of an implant development functional of biological and physiological requirements of the human body, especially the human mouth.

As described above, the rear or ending portion 4 of the implant is tapered, and the rear surface has a slot 6 called fibro-conjunctive slot. The shape of the ending portion as well as the slot 6 are also due to biological and physiological considerations and tests.

The implant 1 is destined for being screwed into a hole of substantially the same diameter which has been drilled before into the jaw by the surgeon. During screwing, the slot 6 serves as a decompression device for coagulated blood which accumulates within said slot. This decompression gives tranquillity to the implant and prevents the patient from irritations and palpitations. In the decompression zone, the coagulated blood is gradually transformed into conjunctive fibers, and after about 6 months, it has become a calcified matter. To resume, the slot allows in a first phase the physiological compensation of matter, and in a second phase a biological retention which is a blocking of the implant by calcified matter. The slot therefore permits first a decompression and hinders then the implant from screwing out during the scarring phase and afterwards.

The tapered portion 4 of the implant allows an easy screwing in by the surgeon. In the embodiment shown in FIGS. 1 to 3, the slot 6 is a V notch. However, the slot may have any desired section, e.g. a squared or U shape. The important feature is that the slot should be made as great as possible, taking the whole diameter of the implant, with the proviso that the solidity of the implant walls in the region of the slot must be respected.

The shape of the threads 5 on the implant is also very important and had also to be selected in function of biological and physiological requirements. The portions 8 and 10 between the surfaces 7 of the turns, having a length of about 1.5 or 2 mm, respectively, are also designed to serve as decompression zones, the implant being held and supported by the surface portions 7. As in the slot 6, coagulated blood accumulates within the thread turns and calcified after a period of about 6 months. This calcified matter firmly blocks the implant so that the resistance to traction will be improved.

The head 2 with its hexagonal shape, having a length of about 5 mm, is arranged to receive a screwing wrench and is also able to optimally distribute the chewing charges on a tooth placed over the implant head. The hexagonal head has a width of about 3.5 mm which is sufficient for a satisfactory mechanical resistance.

The implants having a diameter of 4 to 5 mm may be provided with a circular groove showing in dashed lines 12 in FIG. 1. This groove is located between the hexagonal head 2 and the central portion 3 and permits the gum to better close around the implant under the hexagonal head.

In the variant of FIG. 4, the implant 1 has, as the implant of FIGS. 1 to 3, a hexagonal head 2, a central portion 3 provided with threads 5, and a circular groove 12 under the head 2. Since the implant is made of ceramics, it contains a metallic core 13 imbedded into the ceramics. This core is preferably of stainless steel or of titanium. It can also be made of magnetizable metal as to form a permanent magnet which may serve to attract another metallic or magnetic part (not shown), embedded in a suitable piece, e.g. a crown or a prothesis, to be placed upon the hexagonal head.

The four implant models described above with reference to FIGS. 1 to 4, are made from so-called bioceramics. Bio-ceramics is sapphire or corumdum and has the chemical formula $Al_2O_3$. The implants made from that bio-ceramics have a purity of about 99.7% $Al_2O_3$, a granulation of 2 to 3 $\mu m$, a density of 3.94 gcm$^{-3}$, an elasticity modulus of about $3.10^6$ kg/cm$^2$ ($43.10^6$ psi), a flexural strength of at least 5000 kg/cm$^2$ ($70.10^3$ psi), a knoop hardness of 2000 and a friction coefficient of 0.15. This bio-ceramics is distributed under the Trade name STEMALOX by Rosenthal Technik AG, Lauf (German Federal Republic).

The use of bio-ceramics on the base of alumina is now known to be the best solution for implants since these bio-ceramics are chemically inert in the biological and physiological medium of the human mouth cavity. Furthermore, they have sufficient qualities in terms of hardness and other mechanical resistances. They do not conduct electricity and are not attacked by the different liquids of the human body. The bio-ceramics do further not show rejection phenomena which are a problem with metals.

The implant described above can easily be manufactured by processing from a rod of bio-ceramics. As a variant, it can be made by sintering techniques, known per se, from alumina powder in a suitable mold.

While there have been described above the principles of this invention in connection with specific embodiments, it is to be clearly understood that this description is made only by way of example and not as a limitation to the scope of invention. The implant may be transformed or otherwise improved without departing from the scope of this invention. For instance, the hexagonal head 2 can be replaced by a head having another shape. The number of thread turns 5 can be changed, as it is the shape of the slot 6 which may have a U or square section. The dimensions of lengths, diameter, pitch and thread depth can be changed in function of the intended uses.

The master idea of the invention is believed to be the fact that the new implant has at its lower end a slot or notch as great as possible, and that the end portion of the implant is tapered so that the implant finds its way better than the known ones and will remain in the axis of its hole during screwing. Another important point is the fact that the thread turns are shaped as to leave the maximum of space for the blood and other liquids secreted by the hole walls. These liquids and coagulated blood can therefore be transformed easily to calcified matter and warrant a perfect fixation of the implant in the maxillary bones.

What is claimed is:

1. A bioceramic dental implant for insertion in a prepared opening in the jaw bone for use as a pillar in a patient's mouth, having a head and a central portion provided with a plurality of successive circular recesses, wherein said central portion is generally cylindrically shaped and wherein each of the spires of said recesses on said cylindrical central portion are formed by a supporting cylindrical surface, a truncated conical surface and a concave circular arcuated surface, these three surfaces following one another in the above indicated sequence downwardly on the implant, the concave arcuate surface being following by the surface of the next spire.

2. The implant of claim 1, further comprising a tapered end portion following said central portion and forming an introductory point portion.

3. The implant of claim 1, wherein the end portion is provided with a transversal slot extending substantially over the entire diameter of said end portion.

4. The implant of claim 1 having a total length between 15 mm and 20 mm, a diameter between 4 and 5 mm., and between 2.5 and 7 complete thread spires on said cylindrical central portion.

5. The implant of claim 4 wherein the pitch of the thread is between 1.5 mm and 2 mm.

6. The implant of claim 1, further comprising a metallic core embedded along the longitudinal axis of the dental implant.

* * * * *